Figure 1A:
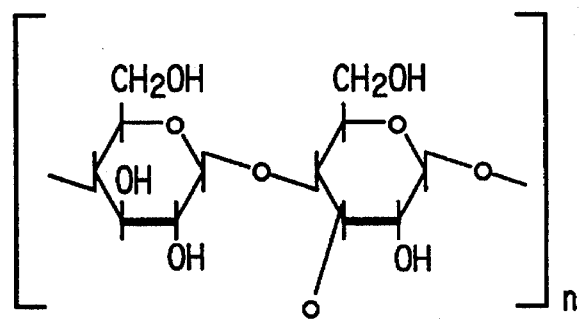

U.S. Patent Number: 5,591,699
Date of Patent: Jan. 7, 1997

Inventor: Richard M. Hodge, Ponca City, Okla.

Assignee: E. I. du Pont de Nemours and Company, Wilmington, Del.

[54] PARTICLE TRANSPORT FLUIDS THICKENED WITH ACETYLATE FREE XANTHAN HETEROPOLYSACCHARIDE BIOPOLYMER PLUS GUAR GUM

[21] Appl. No.: 360,558

[22] Filed: Dec. 21, 1994

Related U.S. Application Data

[63] Continuation-in-part of Ser. No. 21,943, Feb. 24, 1993, abandoned.

[51] Int. Cl.$^6$ .................................................. F21B 43/26
[52] U.S. Cl. .......................... 507/213; 507/110; 536/114
[58] Field of Search .................................. 507/110, 213; 536/114

[56] References Cited

U.S. PATENT DOCUMENTS

| | | | |
|---|---|---|---|
| 3,198,268 | 8/1965 | Lindblom et al. | 175/72 |
| 3,251,417 | 5/1966 | Holman et al. | 166/45 |
| 3,319,715 | 5/1967 | Parks | 166/42 |
| 3,729,460 | 4/1973 | Patton | 260/209 R |
| 3,765,918 | 10/1973 | Jordan et al. | 106/205 |
| 4,033,415 | 7/1977 | Holfmyer et al. | 166/308 |
| 4,105,461 | 8/1978 | Racciato | 252/8.5 X |
| 4,369,124 | 1/1983 | Elphingstone et al. | 252/316 |
| 4,462,917 | 7/1984 | Conway | 252/8.55 R |
| 4,464,270 | 8/1984 | Hollenbeak et al. | 252/8.55 R |
| 4,477,360 | 10/1984 | Almond | 252/8.55 R |
| 4,488,975 | 12/1984 | Almond | 252/8.55 R |
| 4,514,309 | 4/1985 | Wadhwa | 252/8.55 R |
| 4,534,870 | 8/1985 | Williams | 252/8.55 R |
| 4,713,449 | 12/1987 | Vanderslice et al. | 435/104 X |
| 4,798,902 | 1/1989 | Putzig | 556/54 |
| 4,799,550 | 1/1989 | Harris et al. | 166/300 |
| 5,514,791 | 5/1996 | Doherty et al. | 536/114 |

FOREIGN PATENT DOCUMENTS 9219753  11/1992  WIPO.

OTHER PUBLICATIONS

Gray et al., Composition and Properties of Oil Well Drilling Muds, Gulf Publishing Co., Houston, pp. 552–556 and 593 1980.
Jeanes et al., J. Appl. Polym. Sci., vol. 5, pp. 519–526 1961.
Holzwartz, Biochemistry, vol. 15, pp. 4333–4339 1976.
Carbohydrate Research, 57 (1977) 249–272 "Associations Of Like And Unlike Polysaccharides Mechanism And Specificity In Galactomannans, Interacting Bacterial Polysaccharides, And Related Systems," by C. M. Dea et al.
Biochem, J. (1972) 126, 257–272 "Shapely Polysaccharides" by D. A. Rees.
Food Technology, May 1971, vol. 25, 476–483, "Xanthan Gum" by J. K. Rocks.
Carbohydrate Research, 138 (1985) 207–213 "Synergistic Interaction Between Xanthan And Guar Gum" by Masakuni Tako et al.
Polymer Bulletin 14, 157–164 (1985) "The Viscosity Dependence On Concentration, Molecular Weight And Shear Rate Of Xanthan Solutions" by M. Milas et al.

Primary Examiner—Richard L. Raymond
Attorney, Agent, or Firm—James E. Shipley

[57] ABSTRACT

A non-acetylated but otherwise unmodified xanthan heteropolysaccharide polymer plus guar gum, is employed to impart viscosity to an aqueous particle transport fluid (such as a drilling fluid, a fracturing fluid, or a filter structure emplacement fluid) sufficient to suspend mineral particles. A cross linking agent can also be employed to decrease the amounts of xanthan heteropolysaccharide polymer and guar gum which are needed for particle suspension.

8 Claims, 2 Drawing Sheets

X1772

X1773

X1500

X1419

PARTICLE TRANSPORT FLUIDS THICKENED WITH ACETYLATE FREE XANTHAN HETEROPOLYSACCHARIDE BIOPOLYMER PLUS GUAR GUM

CROSS REFERENCE TO RELATED APPLICATIONS

This application is a continuation-in-part of U.S. patent application Ser. No. 08/021,943 filed Feb. 24, 1993, now abandoned.

BACKGROUND OF THE INVENTION

There are extensive publications relating to the use of xanthan heteropolysaccharide biopolymers as viscosifying agents for particle transport fluids such as drilling muds, fracturing fluids, or filter structure emplacement fluids. Early work on xanthan polymers was done at the Northern Regional Research Laboratory of the United States Department of Agriculture at Peoria, Ill. By way of exemplification U.S. Pat. No. 3,198,268 discloses xanthan fermentates being employed in drilling muds and for other oil production uses in 1965. By way of further exemplification, U.S. Pat. No. 3,251,417 discloses xanthan polymers being employed with foaming agents for air drilling.

The xanthan heteropolysaccharide biopolymers produced by *Xanthomonas campestris* and which are widely used in drilling muds and for viscosifying agents in other oil field applications, have been characterized as having the following formula shown in Haworth convention:

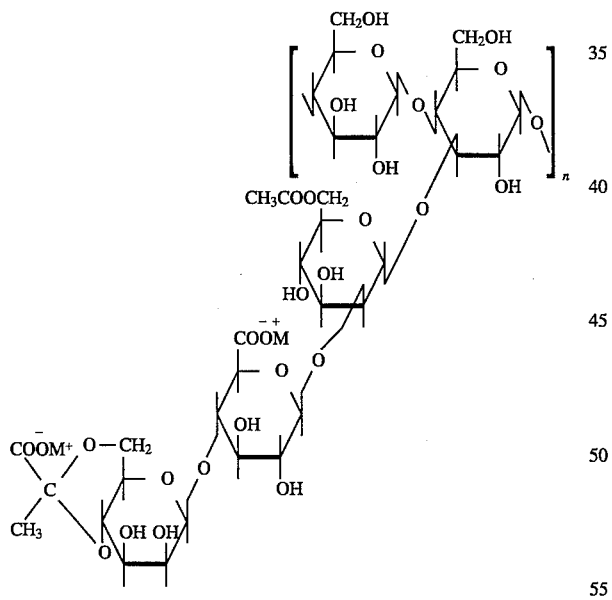

Chemically, the wild or native xanthan polymer is an anionic heteropolysaccharide. The repeating unit of the polymer is a pentamer composed of five sugar moieties, specifically two glucose moieties in the repeating chain unit, two mannose moieties on the side-chains, and a glucuronic acid moiety at the end of the mannose sidechains. Usually, this basic structure is specifically acetylated and pyruvylated as shown and as described for example by Janson, P. E., Kenne, L., and Lindberg, B., in Carbohydrate Research, 45:275–282 (1975) and Melton, L. D., Minot, L., Rees, D. A., and Sanderson, G. R., in Carbohydrate Research, 46:245–257 (1976). The extent of acetylation and pyruvylation is known to vary.

In the formula shown, n can be an integer such that the molecular weight is over 1 million, and $M^+$ is a hydrogen ion or an alkali metal ion such as a sodium ion or a potassium ion.

Xanthan gums find great utility in particle transport fluids such as in drilling muds because a very low concentration, say about 1% solution, imparts pseudoplastic viscosity and keeps mineral particles in suspension. In pseudoplastic systems, the viscosity decreases as the shear rate is increased. This is an instantaneous completely reversible process. Milas, M. et al., Polymer Bulletin 14:157–164 (1985) disclose viscosity dependence of xanthan polymers as a function of polymer concentration, shear rate, and molecular weight.

Reference is also made to U.S. patent application Ser. No. 07/696,732 filed May 7, 1991, now abandoned, by Doherty et at. of Synergen, Inc. entitled "Genetic Control of Acetylation and Pyruvylation of Xanthan Based Polysaccharide Polymers", published 12 Nov. 1992 from International Application Number PCT/US92/03448 and designated International Publication Number WO 92/19753. That reference is specifically referred to and incorporated herein by reference. In particular, the following material is quoted:

"The present invention discloses a family of xanthan based polysaccharides having improved properties relative to naturally-occurring xanthan gum. Modifications of xanthan gum have been previously described. For example, Bradshaw et al. (Carbohydrate Polymers, 3:23–28 (1983) describe methods for preparing chemically modified xanthan gum which is deacetylated or de-pyruvylated. Various means of chemically deacetylating xanthan gum produced by *Xanthomonas campestris* also are described in U.S. Pat. Nos. 3,000,790 and 3,054,689. To date, the predominant method utilized for these deacetylation processes has been chemical removal of the acetate moieties from normally acetylated xanthan gram. It has been found that chemical processes for deacetylating xanthan gums can result in a number of undesirable side effects and may cause hydrolysis of the glycosidic backbone, resulting in an irreversible change in the conformation of the molecule and lowered molecular weight.

Some of the rheological properties of deacetylated xanthan in aqueous media are known. See, e.g., Tako and Nakamura, Agric. Biol. Chem.48:2987–2993 (1984) and U.S. Pat. Nos. 3,000,790 and 3,054,689. Also, a method of increasing the viscosity of an aqueous solution using a deacetylated polysaccharide is described in U.S. Pat. No. 3,096,293. Thus, a method for obtaining non-acetylated xanthan which does not cause untoward side effects has been sought.

Xanthan gum can be chemically de-pyruvylated as well, as described by Holzwarth and Ogletree in Carbo. Res. 76:277–280 (1979). This chemical method of de-pyruvylation also can alter the xanthan polymeric unit and/or cause hydrolysis of the glycosidic backbone. While a strain of *X. campestris* has been described in U.S. Pat. No. 4,296,203 which produces non-pyruvylated xanthan gum, this non-pyruvylated gum was either fully acetylated or deacetylated using chemical means.

Additionally, the extent of acetylation of the internal mannose on the xanthan side chain and the extent of the pyruvylation of the terminal mannose may vary. The present inventors believe that a fully acetylated and/or fully pyruvylated xanthan will have improved rheological properties for certain oil recovery properties.

Moreover, the present inventors have identified polysaccharides which are based on alterations of the normal xanthan pentamer building block."

Figure 1A:
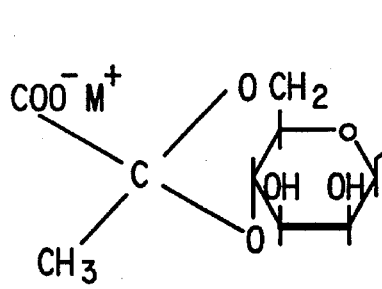
Figure 1A:
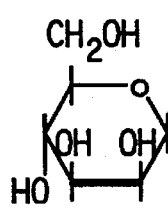
Figure 1B:
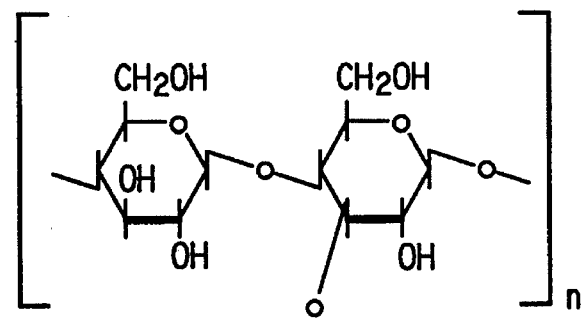
Figure 1C:
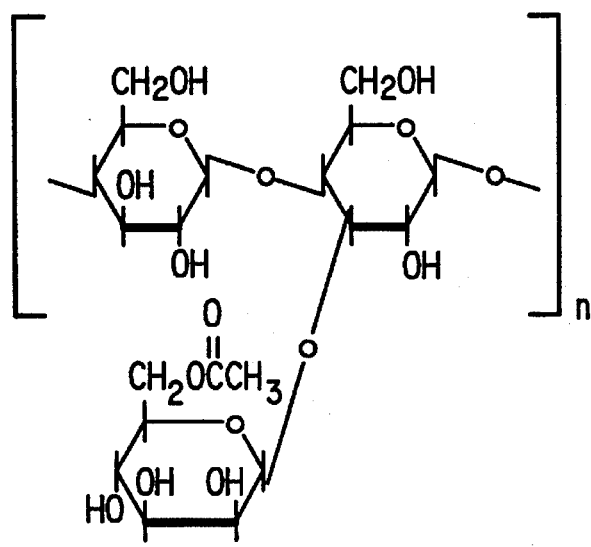
Figure 1D:
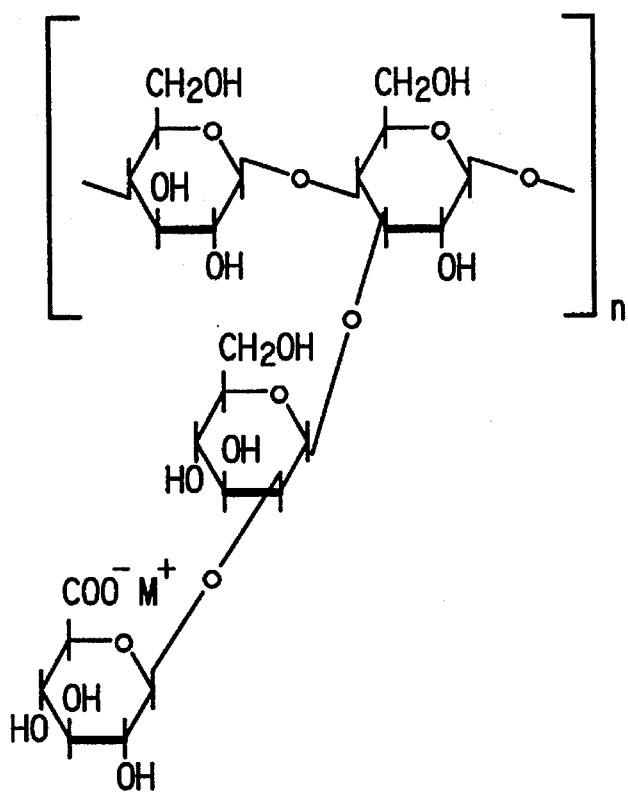

Summarily, the Synergen reference discloses biosynthesis of polymers having structures as shown in FIG. 1.

A series of patents are exemplary of the state of the art relating to the use of wild or native xanthan polymers in fluids for oil patch applications. For example, U.S. Pat. No. 3,319,715 discloses the use of $Mg(OH)_2$ plus wild or native xanthan polymer as a fluid loss additive for fluids employed as drilling fluids, reworking fluids, perforating fluids, fracturing fluids, etc. U.S. Pat. No. 3,729,460 discloses improved thickening to be obtained from xanthan polymers by heating with an alkali metal hydroxide compound.

Another series of references discloses use of cross linked viscous compounds such as guar gum, locust bean gum, etc. as thickened fluids for use in oil production operations. For example, U.S. Pat. No. 4,033,415; U.S. Pat. No. 4,369,124; U.S. Pat. No. 4,534,870; U.S. Pat. No. 4,462,917; U.S. Pat. No. 4,464,270: U.S. Pat. No. 4,488,975; U.S. Pat. No. 4,798,902; U.S. Pat. No. 4,799,550; U.S. Pat. No. 4,477,360; and U.S. Pat. No. 4,514,309 disclose use of a variety of cross linking agents to prepare cross linked polysaccharides and to prepare a variety of thickened fluids employed in oil field applications.

None of the foregoing references appear to disclose or suggest use of a non-acetylated but otherwise unmodified xanthan heteropolysaccharide polymer plus guar gum to impart viscosity to an aqueous particle transport fluid sufficient to suspend mineral particles, as is disclosed and claimed according to the invention at hand, however. By "non-acetylated" xanthan we mean xanthan produced without an acetyl group by biosynthesis such as by the Synergen reference above and having the structure shown in FIG. 1. In contrast, by "deacetylated" xanthan we mean xanthan which has had its acetyl group removed by chemical or other means.

The following disclosures are of particular relevance to the invention at hand:

Dea, I. C. M. and Morris, E. R, "Synergistic Xanthan Gels", (inventor/ACS Symposium Series, 45 (1977) 174–181) disclose that native xanthan polymer does not form a gel, but on mixing with locust bean gum, another non gelling polysaccharide, firm rubbery gels are formed at low polymer levels. It is also disclosed that guar gum does not gel with xanthan polymer in any concentration and that weaker gels are obtained with gum tara. Molecular explanations for the strange phenomena are provided.

Dea, I. C. M., Morris, E. R., Rees, D. A., Welsh, E. J., Barnes, E. A., and Price, J., "Associations of Like and Unlike Polysaccharides Mechanism and Specificity in Galactomannans, Interacting Bacterial Polysaccharides, and Related Systems", Carbohydrate Research, 57 (1977) 249–272 also disclose that locust bean gum gels with native xanthan polymers and a xanthan polymer alone does not gel at any concentration. The reference also discloses that guar gum does not gel at all when mixed with xanthan polymer. Various molecular theories are proposed to explain the phenomenon.

Much the same disclosure is made by Rees, D. A. "Shapely Polysaccharides", Biochem, J. (1972) 126, 257–272.

Much the same disclosure is also made by Rocks, J. K., "Xanthan Gum" (inventor/Food Technology, 25 (1971) 476–485).

Perhaps the closest reference to the invention at hand of which the inventor is aware is that of Tako, M., Nakamura, S., "Synergistic Interaction Between Xanthan and Guar Gum", Carbohydrate Research, 138 (1985) 207–213. In particular, FIG. 3 on Page 211 plots dynamic viscoelasticity of mixtures of guar gum and native xanthan polymer and of guar gum and deacetylated xanthan polymer. FIG. 3 shows the effect at 25° C. of the ratio of xanthan (native and deacetylated) to guar gum in solution on the dynamic viscoelasticity of a total gum concentration of 0.2%. In the case of the mixture with native xanthan, little synergistic increase in dynamic viscoelasticity is observed. However, the synergistic interaction was enhanced in the mixture with deacetylated xanthan, indicating the intermolecular interaction resulted from deacetylation of xanthan. FIG. 3 shows the maximum dynamic modulus was achieved when the mixing ratio of deacetylated xanthan to guar gum was 2:1.

The deacetylated xanthan polymer employed is stated to be chemically deacetylated, which means that it is otherwise modified by the chemical deacetylation procedure. Even though the results reported in the article do show a synergistic interaction in increasing high shear viscosity, the synergistic interaction is not in any way predictive of the much greater and different effect of suspending mineral particles at very low shear obtained according to the invention at hand which is disclosed and claimed in this application.

In other words, prior art fluids can be formulated with higher shear viscosities which are equivalent to the fluids of this application, but these fluids do not suspend particles any where nearly as effectively as the fluids of this application, as demonstrated by the runs disclosed in this application.

SUMMARY OF THE INVENTION

In accordance with the invention of application, the inventor has discovered that a quite small amount of non-acetylated but otherwise unmodified xanthan heteropolysaccharide polymer plus a quite small amount of guar gum can be employed to impart viscosity to an aqueous particle transport fluid (for example, a drilling fluid, fracturing fluid, or a filter structure emplacement fluid) sufficient to suspend mineral particles. A cross linking agent can also be employed to further decrease the amount of non-acetylated xanthan, heteropolysaccharide polymer and guar gum which are needed for particle suspension. The non-acetylated xanthan variants of this invention have the following formula as shown in Haworth convention following and in FIG. 1:

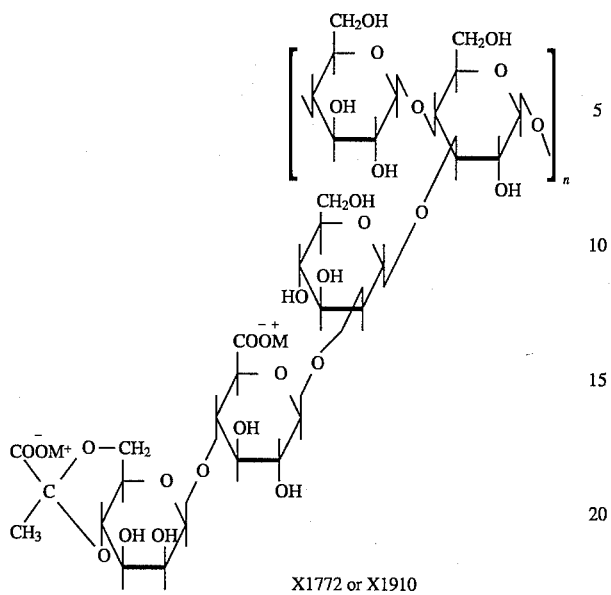

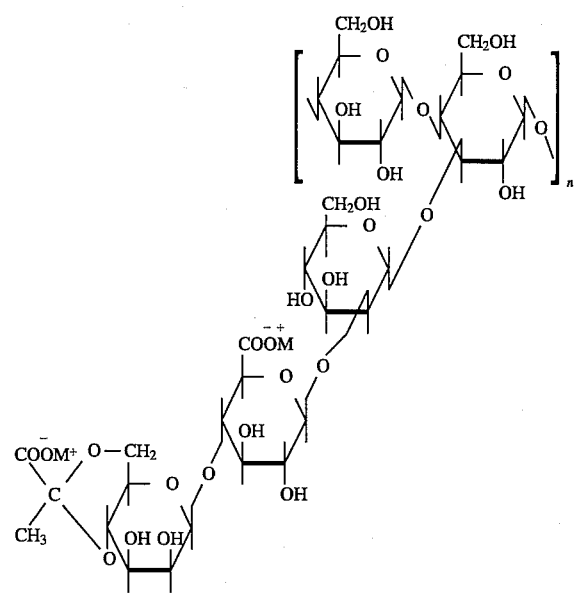

wherein M⁺ can be a cation such as a hydrogen ion or an alkali metal ion, for example, a sodium ion or a potassium ion.

The foregoing xanthan polymers can be produced by a *Xanthomonas campestris* variant such as that having Accession Number 68038 at the American Type Culture Collection, Rockville, Md., or by a mutant *Xanthomonas campestris* variant having a suitable chromosomal deletion mutation. The xanthan polymer variants which are suitable according to this invention are quite specific. For example, xanthan polymers produced by native or wild *Xanthomonas campestris* are nowhere nearly as effective in suspending particles, nor are other variants produced by genetic engineering means, nor are conventional xanthan polymers which are deacetylated by chemical means.

The viscous aqueous particle transport fluid of this invention must comprise water and a small but suspending amount of the non-acetylated but otherwise unmodified xanthan heteropolysaccharide polymer specified herein. One example of such an aqueous particle transport fluid is a drilling mud. Such drilling muds can comprise other materials as are well known to those skilled in the drilling art, such as clays, salts such as sodium chloride, etc. Of course, upon use, such drilling muds will contain mineral particles such as drill cuttings which are held in suspension by the xanthan polymers of the invention. Additionally, such drilling muds can contain lubricating agents such as hydrocarbons, polyesters, other thickening agents, etc. as are known in the highly developed art of drilling muds.

Other examples of viscous aqueous particle transport fluids of the invention, in addition to drilling muds, include fracturing fluids and fluids employed to emplace filtering structures. In such cases, the fluids can also comprise propping agents such as ceramic beads, sand, gravel, and the like as are known in these arts, as well as other components which are conventionally employed in these arts, such as epoxy systems which set up to bind the sand or gravel particles into a suitable porous filtering structure.

The viscous aqueous particle transport fluids of this invention must comprise (1) water, (2) a small amount of guar gum, and (3) a small amount of a xanthan heteropolysaccharide polymer having the following formula in Haworth convention:

wherein M⁺ can be a hydrogen ion or an alkali metal ion and wherein the amount of guar gum employed plus the amount of xanthan heteropolysaccharide polymer employed is sufficient to suspend mineral particles. However, the amount of guar gum and the amount of xanthan heteropolysaccharide polymer is not sufficient to suspend the mineral particles if employed alone. Optimal amounts for each particular viscous aqueous particle transport fluid employed can readily be determined by those skilled in the art by experimentation not amounting to invention. Other components of each viscous aqueous particle transport fluid will determine the amount of non-acetylated xanthan heteropolysaccharide polymer which is optimally employed and the amount of guar gum which is optimally employed. The particular use for which the particular fluid is employed as well the costs of the respective materials will also affect the amounts.

Examples of some presently preferred crosslinking agents include:

| Borate compounds | Titanium complexes | Zirconium complexes |
|---|---|---|
| Boric Acid | DuPont's "Tyzor TE," | Lactates |
| Borax | "AA," "LA," "101," | Triethanolamine |
| Ulexite | and "131" | Acetylacetonate |
| Colemanite | | |
| Borate complexes | | |
| (U.S. Pat. No. 5,082,579) | | |

Amounts of guar gum in the range of about 0.08 to 1.0 weight percent of the viscous aqueous particle transport fluid and amounts of non-acetylated xanthan heteropolysaccharide polymer in the range of about 0.02 to 0.25 are often suitable.

EXAMPLES

In accordance with a presently preferred mode of this invention, the non-acetylated but otherwise unmodified xanthan heteropolysaccharide polymers of the invention are prepared as disclosed in International Publication Number WO 92/19753 based on U.S. patent application Ser. No. 07/696,732 filed May 7, 1991, now abandoned, by Doherty et al. of Synergen Inc. entitled "Genetic Control of Acetylation and Pyruvylation of Xanthan Based Polysaccharide Polymers," herewith incorporated by reference.

More specifically, a mutant of *Xanthomonas campestris* which produces suitable polymers which are unmodified (non-acetylated) at the inner mannose and pyruvylated at the outer mannose has been placed on deposit at the American Type Culture Collection, Rockville, Md., under Accession Number 68038. By way of further example, xanthan variant polymers produced by isolate X1910 can also be employed in accordance with this invention and are indistinguishable from wild type xanthan with respect to glucose, mannose, glucuronic acid and pyruvate, but have no acetate. Mutant X1910 produces non-acetylated xanthan equivalent to that produced by variant X1402 (Accession Number 68038) or variant 1772 but does so as a result of the chromosomal deletion mutation. No recombinant plasmid or any foreign DNA is present in this strain. Mutant X1910 is described in Example 5 of the Synergen reference and produces the same xanthan heteropolysaccharide polymer which is disclosed and claimed in this application.

Native or wild xanthan polymer and the other xanthan variants which were tested in comparison to the non-acetylated but otherwise unmodified xanthan heteropolysaccharide polymer of this invention were also produced in accordance with the disclosure of U.S. patent application Ser. No. 07/696,732, now abandoned. The "Xan Vis" polymer is a purified commercial product obtained from Kelco Division of Merck & Co. Inc., and is a well known item of commerce generally available in the oil industry.

Structures of polymers equivalent to the Synergen designations are shown in FIG. 1. Generally, X1772, X1402, and X1910 are equivalent and are the xanthan variant polymers of this invention. Generally, "Xan Vis" polymer and the polymer designated by Synergen as X1309 are native or wild xanthan polymer and are equivalent thereto.

As illustrated by earlier work (Tako, M. and Nakamura, S.), the synergistic interaction between deacetylated xanthan and guar gum produces an increase in viscosity with the optimum ratio of deacetylated xanthan to guar being about 2:1 (w/w). A synergistic increase in viscosity was also obtained with X1910:guar mixtures as illustrated in Table 1.

TABLE 1

Viscosity of X1910:Guar Mixtures at 75° F.

| X1910 Conc (% by wt) | Guar Conc (% by wt) | Apparent Viscosity (cp) @ 3.4 s$^{-1}$ |
|---|---|---|
| 0.24 | 0 | 900 |
| 018 | 0.06 | 676 |
| 0.12 | 0.12 | 902 |
| 0.06 | 0.18 | 1052 |
| 0.05 | 0.19 | 1353 |
| 0 | 0.24 | 150 |

Furthermore, the viscosity of the X1910:guar gum mixture is greater than the viscosity of either guar or guar:native xanthan solution at the same total polymer concentration (0.24% w/w) as illustrated in Table 2.

TABLE 2

Viscosity of 0.24% (w/w) Polymer Solutions at 75° F.

| | X1910:Guar @ 1:4 (w/w) | Guar | "Xan Vis": Guar @ 1:4 (w/w) |
|---|---|---|---|
| Visc (cp) @ 34 s$^{-1}$ | 43 | 13 | 15 |

The results show the viscosity of the 1:4 (w/w) X1910:guar mixture was significantly higher than either the guar or 1:4 guar:"Xan Vis" solution. This finding is consistent with the references cited earlier showing the synergistic increase in viscosity obtained by mixing guar and deacetylated xanthan. However, by crosslinking these same polymer solutions, the viscosity increase due to synergistic interaction between the non-acetylated xanthan and guar is no longer evident. Table 3 compares viscosity values obtained after the addition of varying amounts of $H_3BO_3$ crosslinker. All polymer solutions contained 2% KCl (w/w), 0.12% $NaHCO_3$ (w/w), and 0.15% $Na_2CO_3$ (w/w). Viscosity measurements were performed with a Farm 50C viscometer using an R1 rotor and B1 bob.

TABLE 3

Viscosity of 0.24% (w/w) Polymer Solutions at 75° F.

| % $H_3BO_3$ (w/w) | X1910:Guar (1:4) | Guar | "Xan Vis": Guar (1:4) |
|---|---|---|---|
| 0 | 43 | 13 | 15 |
| 0.003 | 34 | 18 | 22 |
| 0.009 | 79 | 74 | 43 |
| 0.015 | 411 | 326 | 85 |
| 0.018 | 382 | 385 | 59 |
| 0.021 | 468 | 441 | 449 |
| 0.027 | 324 | 197 | 258 |
| 0.033 | 125 | 106 | 66 |

These results show the maximum crosslinked viscosity was obtained at a $H_3BO_3$ concentration of 0.021% (w/w). Furthermore, the peak, crosslinked viscosity for each polymer solution was nearly equal.

Based on these results (i.e., equivalent peak, crosslinked viscosities), one might expect the suspending properties of the polymer solutions at 0.021% $H_3BO_3$ to be equivalent. However, examination of particle settling rates in these solutions showed the crosslinked mixture of X1910 and guar provided an unexpected improvement in particle suspension although the viscosities of the three crosslinked solutions were nearly equal. The results of the particle setting test are contained in Table 4. A standard method for measuring particle settling rate (API RP39 Second Edition January 1983) was used to examine the particle suspending properties of these crosslinked polymer solutions. Rather than using sand, a ceramic proppant (CARBO CERAMICS INC. Carbo-Prop® HC 16/30 Mesh) was used throughout the testing.

TABLE 4

Particle Settling Rates (inches/minute) for 0.24% (w/w) Polymer Solutions at 75° F.

| % $H_3BO_3$ (w/w) | X1910:Guar (1:4) | Guar | "Xan Vis": Guar (1:4) |
|---|---|---|---|
| 0 | 12.73 | 168 | 48 |
| 0.003 | 8.18 | 151 | 3.18 |
| 0.009 | 0.01 | 47 | 0.29 |

TABLE 4-continued

Particle Settling Rates (inches/minute) for 0.24% (w/w) Polymer Solutions at 75° F.

| % $H_3BO_3$ (w/w) | X1910:Guar (1:4) | Guar | "Xan Vis": Guar (1:4) |
|---|---|---|---|
| 0.015 | 0.0013 | 0.9 | † |
| 0.018 | 0.008 | 0.6 | 0.017 |
| 0.021 | 0.003 | 0.09 | 0.013 |
| 0.027 | 0.002 | * | 0.009 |
| 0.033 | 0.001 | * | * |

\* - Syneresis occurred during test
† - Polymer agglomeration without formation of free water occurred during tests These results show the crosslinked mixture of X1910:Guar provides superior particle suspension when compared to crosslinked polymer solution containing either guar or a mixture of "Xan Vis" and guar.

Details of the foregoing runs follow:

Polymer solutions in Table 1 were prepared as follows:

Polymer solutions were prepared as 0.36% (w/w) stock solutions of X1910 and guar (Halliburton WG19). Each stock solution contained 2000 ppm formaldehyde and 0.1 moles per liter NaCl. Aliquots of the stock solutions were mixed together to produce the desired X1910:guar ratio. The total polymer concentration was obtained by adding a diluent containing 0.1M NaCl and 2000 ppm formaldehyde.

Viscosity measurements were performed at 75° F. with a Baroid Multispeed Viscometer with standard Rotor and Bob geometry.

Polymer solutions in Tables 2–4 were prepared as follows:

Polymer solutions of X1910, guar (Halliburton WG19), and Kelco "Xan Vis" were prepared as 0.24% (w/w) solutions in deionized water containing 2.0% (w/w) KCl. Addition of 0.006% (w/w) fumaric acid was added to the guar solution to promote polymer hydration. The pH of all polymer solutions was adjusted to about 9.8 by adding 0.12% (w/w) $NaHCO_3$, and 0.15% (w/w) $Na_2CO_3$. The Boric acid crosslinker was then added to each polymer solution as a 3% (w/w) solution to obtain the desired $H_3BO_3$ concentration.

The viscosity of the polymer solutions was measured with a Farm 50C viscometer using the R1B 1 rotor/bob combination. Each polymer solution was sheared at shear rates of 34, 68, 102, 136, 170, 136, 102, 68, and 34 $s^{-1}$. The final 34 $s^{-1}$ shear stress value was used to calculate the apparent viscosities reported in Tables 2–4.

Elevated temperature formulation:

Fluid composition (all concentrations in weight %):
FLUID #1 X1910 0.048

| Guar (Halliburton WG19) | 0.192 |
|---|---|
| $Na_2CO_3$ | 0.08 |
| $NaHCO_3$ | 0.06 |
| Formaldehyde | 0.1 |
| NaCl | 0.58 |
| $H_3BO_3$ | 0.027 |

FLUID #2 Guar (Halliburton WG19) 0.24

| $Na_2CO_3$ | 0.08 |
|---|---|
| $NaHCO_3$ | 0.06 |
| Formaldehyde | 0.1 |
| NaCl | 0.58 |
| $H_3BO_3$ | 0.027 |

Viscosity measured with a Farm 35 using R1B1 rotor/bob combination at a shear rate of 5.1 $s^{-1}$ Results

| | Viscosity @ 5.1 $s^{-1}$ | |
|---|---|---|
| | 110 F. | 140 F. |
| FLUID #1 | 1700 cp | 900 cp |
| FLUID #2 | 1700 cp | 250 cp |

I claim:

1. A viscous aqueous particle transport fluid comprising:
   (a) water,
   (b) from about 0.08 to 1.0 weight percent of guar gum, and
   (c) from about 0.02 to 0.25 weight percent of a non-acetylated but otherwise unmodified xanthan heteropolysaccharide polymer having the following formula in Haworth convention:

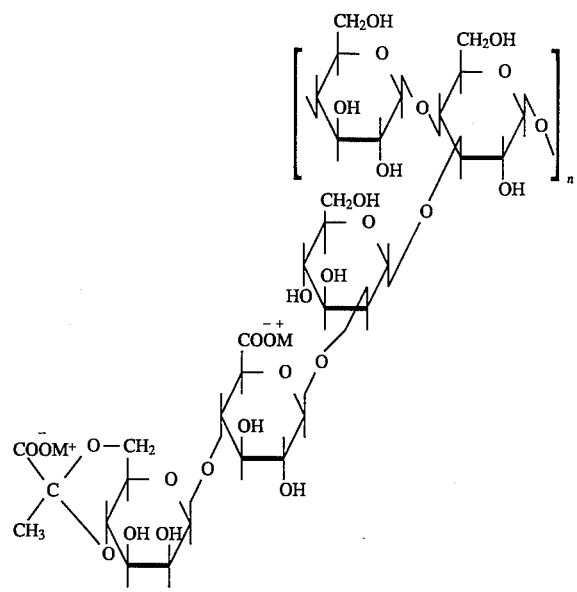

wherein $M^+$ can be a hydrogen ion or an alkali metal ion and wherein the ratio of guar gum employed to the amount of xanthan heteropolysaccharide polymer employed is between about 2:1 to about 5:1.

2. The fluid of claim 1 (twice amended) wherein $M^+$ is a sodium ion or a potassium ion, wherein the molecular weight of the xanthan heteropolysaccharide polymer is in the range of about one million to about 15 million, and wherein the particle transport fluid is a drilling mud, a fracturing fluid, or a filter emplacement fluid.

3. The fluid of claim 2 wherein the xanthan polymer is produced by a *Xanthomonas campestris* variant having Accession Number 68038 at the American Type Culture Collection, Rockville, Md., or by a mutant *Xanthomonas campestris* variant having a suitable chromosomal deletion mutation.

4. The drilling fluid of claim 2 wherein the drilling fluid also comprises mineral particles held in suspension.

5. The particle transport fluid of claim 1 which comprises a fracturing fluid, which also comprises mineral particles held in suspension, and wherein $M^+$ is a sodium ion or a potassium ion, and wherein the molecular weight of the xanthan heteropolysaccharide polymer is in the range of about 1 million to about 15 million.

6. The aqueous particle transport fluid of claim 1 which also comprises from about 0.0015 to 0.1 weight percent of a borate cross linking agent.

7. The fluid of claim 6 wherein $M^+$ is a sodium ion or a potassium ion, wherein the molecular weight of the xanthan heteropolysaccharide polymer is in the range of about 1 million to about 15 million, and wherein smaller quantifies of xanthan heteropolysaccharide polymer plus guar gum are present than would suspend mineral particles if no cross linking agent were present.

8. The fluid of claim 7 wherein the xanthan heteropolysaccharide polymer is present in the range of about 0.02 to about 0.25 weight percent of the fluid, wherein guar gum is present in the range of about 0.08 to about 1.0 weight percent of the fluid, and wherein the cross linking agent is present in the range of about 0.0015 to about 0.10 weight percent of the fluid.

* * * * *